(12) United States Patent
Hermansson et al.

(10) Patent No.: US 7,867,329 B2
(45) Date of Patent: Jan. 11, 2011

(54) DENTAL CEMENT SYSTEM, A POWDERED MATERIAL AND A HYDRATION LIQUID THEREFOR, AND CERAMIC MATERIAL FORMED THEREFROM

(75) Inventors: Leif Hermansson, Mölle (SE); Jesper Lööf, Uppsala (SE); Håkan Engqvist, Knivsta (SE)

(73) Assignee: DOXA AB, Uppsala (SE)

( * ) Notice: Subject to any disclaimer, the term of this patent is extended or adjusted under 35 U.S.C. 154(b) by 667 days.

(21) Appl. No.: 11/895,232

(22) Filed: Aug. 23, 2007

(65) Prior Publication Data

US 2009/0050015 A1    Feb. 26, 2009

(51) Int. Cl.
*C04B 7/32* (2006.01)
(52) U.S. Cl. .......................... 106/35; 106/692
(58) Field of Classification Search .................. 106/35
See application file for complete search history.

(56) References Cited

FOREIGN PATENT DOCUMENTS

| EP | 0 241 277 | 10/1987 |
|---|---|---|
| EP | 0 559 627 A2 | 9/1993 |
| WO | WO 90/11066 A1 | 10/1990 |
| WO | WO 00/21489 A1 | 4/2000 |
| WO | WO 01/76534 A1 | 10/2001 |
| WO | WO 01/76535 A1 | 10/2001 |
| WO | WO 03/041662 A1 | 5/2003 |
| WO | WO 03/055450 A1 | 7/2003 |
| WO | WO 2004/037215 A1 | 5/2004 |
| WO | WO 2005/039508 A1 | 5/2005 |

OTHER PUBLICATIONS

PCT International Search Report (Form PCT/ISA/210) dated Apr. 25, 2008 in corresponding PCT Application PCT/SE2007/050574.
Written Opinion of the International Searching Authority (Form PCT/ISA/237) dated Apr. 25, 2008 in PCT in corresponding Application PCT/SE2007/050574.

*Primary Examiner*—Paul Marcantoni
(74) *Attorney, Agent, or Firm*—Lucas & Mercanti, LLP; Robert P. Michal

(57) ABSTRACT

A dental cement system, including an aqueous hydration liquid and a powdered material that essentially consists of an inorganic cement system, which powdered material has the capacity to form a complex, chemically bonded material with inorganic as well as organic phases with properties suitable for cementation of implant to another implant and/or to tooth or bone tissue.

27 Claims, No Drawings

DENTAL CEMENT SYSTEM, A POWDERED MATERIAL AND A HYDRATION LIQUID THEREFOR, AND CERAMIC MATERIAL FORMED THEREFROM

TECHNICAL FIELD

The present invention relates to a cement system, comprising an aqueous hydration liquid and a powdered material that essentially consists of an inorganic cement system, which powdered material has the capacity to form a complex, chemically bonded material with inorganic as well as organic phases with properties suitable for cementation of implant to another implant and/or to tooth or bone tissue. The invention relates to the powdered material and the hydration liquid, respectively, as well as the formed ceramic material and a kit comprising the system.

STATE OF THE ART AND PROBLEM

The present invention relates to dental cement systems of the hydrating cement system type, and more particularly cement-based systems that comprise chemically bonded ceramics of aluminates, and optionally additional chemically bonded phases such as silicates, phosphates, carbonates, sulphates and combinations thereof, having calcium as the major cation. The invention has been especially developed for biomaterials for dental cement applications (fillers and cement)—but other applications also comprise orthopedic applications, both fillers and cements as well as implants including coatings and carriers for drug delivery.

For materials, such as dental cement materials and other implants, that are to interact with the human body, the materials should be as bioactive or biocompatible as possible. Other properties that are required for dental cement materials are a good handling ability with simple applicability, moulding that permits good shaping ability, hardening/solidification that is sufficiently rapid for use within minutes without detrimental heat generation and that provides serviceability directly following therapy, corrosion resistance, good bonding between the cement material and biological wall and/or implant material, radio-opacity, good long time properties and good aesthetics especially regarding dental filling materials. Materials fulfilling at least most of these required properties, are known in the art and have been described in e.g. WO 90/11066, EP 559 627 A2, WO 00/21489, WO 01/76534, WO 01/76535, PCT/SE02/01480 and PCT/SE02/01481.

WO 2005/039508 relates to a system for chemically bonded ceramic (CBC) materials, preferably a dental filling material or an implant material, comprising a two-step procedure. The system includes an initial working part-system to provide for improved early-age properties and a second main system to provide for improved end-product properties including bioactivity. The systems interact chemically. The main system is of the hydrating cement system type, in particular cement-based systems that comprise chemically bonded ceramics in the group that consists of aluminates, silicates, phosphates, carbonates, sulphates and combinations thereof, having calcium as the major cat-ion, while the initial working part system comprises polyacrylic acid and/or a salt thereof or other polycarboxylic acids, co-polymers thereof, or polycarboxylates (i.e. a salt or ester of a polycarboxylic acid). For dental applications the polycarboxylic acid or a copolymer or a salt or an ester thereof, is preferably used in an amount of 3-15% by weight, based on the powdered material including any dry additives, and for orthopedic applications in 2-5% by weight.

SUMMARY OF THE INVENTION

The present invention specifically relates to materials which exhibit the following main criteria, namely chemical composition of both the powder and the liquid for a functioning product with specified intended use, where bioactivity and very limited microleakage are improved in comparison to other materials. Furthermore the invention describes additions of chelating agents with neutral pH to the mixing liquid yielding unique setting properties which allow for compliance both with low film thickness demands and with the requirement of reasonable setting times. A further aspect of the invention deals with the robustness of the materials property over a wider powder to liquid ratio range. According to the present invention the addition of $Na_3$-NTA to the liquid also gives a robustness in properties over a wider P:L ratio range compared to a liquid without it. This gives the opportunity to utilise a capsule mixing system.

In one aspect the present invention relates to a cement system having improved bioactivity and very limited microleakage, which system comprises (a) a powdered cement comprised of 40-60 wt % of calcium aluminate, 8-15 wt % of poly acrylic acid, 0.5-5 wt % of tartaric acid, 25-45 wt % of strontium-fluoro-alumino-silicate glass, and 2.5-10 wt % of strontium fluoride; and (b) an aqueous hydration liquid based on deionized water.

In one embodiment the inventive system fulfilling the basic requirements of ISO 9917:2003 the system exhibits a ratio of powdered cement to aqueous hydration liquid (P:L) from 2.0:1 up to 4.0:1.

In a further embodiment a cement system especially suitable for use with a conventional capsule mixing and dispensing device, having very stable net setting time (ST), film thickness (Ft), and compressive strength (CS) is provided, which system exhibits a P:L ratio of from 3.0:1 to 3.7:1, and more preferably from 3.0:1 to 3.6:1.

In another aspect the present invention relates to a powdered cement for use in the inventive system, the cement comprising 40-60 wt % of calcium aluminate, 8-15 wt % of poly acrylic acid, 0.5-5 wt % of tartaric acid, 25-45 wt % of strontium-fluoro-alumino-silicate glass, and 2.5-10 wt % of strontium fluoride.

In one embodiment a powdered cement especially suitable for use as a dental luting cement for thin layers (10-20 µm) is provided, comprising 47-68 wt % of calcium aluminate, 11-12 wt % of poly acrylic acid, 1.5-2.0 wt % of tartaric acid, 33-35 wt % of strontium-fluoro-alumino-silicate glass, and 4-6 wt % of strontium fluoride.

In a further aspect the present invention relates to a hydration liquid for use in the cement system, especially suitable for a dental luting cement for thin layers (10-20 µm), comprising 98-100 wt % of deionised water, 10-200 mM of LiCl, and 0.1-2 wt % of a $Ca^{2+}$ scavenging chelating agent.

In one embodiment of the inventive hydration liquid the $Ca^{2+}$ scavenging chelating agent is selected from the group consisting of partially or fully neutralized nitrilo tri acetic acid (NTA), or a mixture thereof.

In a further aspect the present invention relates to a kit comprising the inventive cement system, i.e. the powdered cement and the hydration liquid In yet a further aspect the present invention relates to a capsule mixing system containing the cement system of the invention.

In yet a further aspect the present invention relates to the use of the cement system of the invention for cementation of an implant to another implant and/or to tooth or bone tissue.

Further aspects, embodiments and advantages will become apparent from the detailed description, examples and appended claims.

DETAILED DESCRIPTION OF THE INVENTION

The present invention relates to a dental luting cement intended for permanent cementation of porcelain fused to metal crowns, all metal crowns, inlays and onlays, fiber reinforced resin composite restorations and allceramic restorations made of high strength aluminous oxide or zirconium oxide, as well as a cementation of an implant material to tooth structure.

The material is designed as a powder, which is also referred to as powdered cement, and a liquid, which is also referred to as hydration liquid, respectively, which liquid is mixed with the powder to make up the final material. The main ingredients of the powder are: calcium aluminate, polyacrylic acid, partaric acid, strontium-fluoro-alumino-glass and strontium fluoride.

In its most generic form the powdered cement of the invention is comprised of: calcium aluminate 40-60 wt %, poly acrylic acid 8-15 wt %, tartaric acid 0.5-5 wt %, strontium-fluoro-alumino-silicate glass 25-45 wt %, and strontium fluoride 2.5-10 wt %.

Within the range of 40-60% by weight of calcium aluminate the calcium aluminate may optionally comprise additional chemically bonded phases having calcium as the major cation, such as silicates, phosphates, carbonates, sulphates and combinations thereof, in an amount of maximally up to the upper limit of 60% by weight. That is to say that according to the invention the calcium aluminate is present in an amount of at least 40% by weight and that, if present, any of the above additional phases are used in a total amount of up to 20% by weight, with the proviso that the total amount of calcium aluminate and any such additional phases may not exceed 60% by weight. Especially for dental applications it is however preferred that only calcium aluminate is present.

According to the invention the powder components exhibit the following characteristics: The calcium aluminate has a particle size below 12 μm with a mean particle size in the range of 1.5-4 μm. The calcium aluminate preferably has a phase composition with at least 95% monocalcium aluminate and below 1% mayenite. According to preferred embodiments of the invention the strontium fluoro alumino silicate glass is pre-treated in order to lower the reactivity of the glass. This can preferably be done by etching the glass with acetic acid for an appropriate period of time depending on the reactivity required. The strontium fluoride has a maximum particle size in the range of the medium particle size of the Ca aluminate.

In its most generic form a suitable hydrating liquid for the above powdered cement comprises deionised water.

In order to obtain an early compressive strength, LiCl should be included in the hydrating liquid, preferably in a concentration of 10-200 mM.

In a preferred embodiment the hydration liquid comprises the following main components: 15-18 mM LiCl, 0.2-0.4 wt % tri sodium nitrilo tri acetic acid ($Na_3$-NTA) and balance deionised water to 100%.

The inventive powder and liquid can be mixed in a wide variety of P:L ratios (powder:liquid). The powder and liquid described herein may be mixed in a P:L ratio ranging from 2.0:1-4.0:1 and still fulfil the basic requirements of the ISO 9917:2003. This is made possible by the addition of NTA to the liquid. Comparative tests without NTA do not comply with the ISO 9917:2003.

The function of the poly acrylic acid or a salt thereof can be divided into cross-linking and dispersing abilities. Upon mixing of the powder and liquid components of the invention the powdered calcium aluminate material will first dissolve in the liquid, thereafter Ca- and Al-ions will cross-link the polyacrylic acid to form a polyacrylate polymer, and other Ca- and Al-ions will hydrate to form a hydrated calcium aluminate material in a second step. The resulting, hydrated material is a composite of chemically bonded ceramic material and a cross-linked polyacrylate polymer.

In case of a dental cement a preferred average molecular weight of the polyacrylic acid is at least 5,000, such as from 5,000 to 100,000. For other applications of the invention polyacrylic acid of a higher average molecular weight could be used, such as up to 250,000.

The product is a hybrid between a glass ionomer cement (GIC) and calcium aluminate. The glass ionomer part is essentially responsible for early properties, i.e. viscosity, setting time, early strength and pH. The calcium aluminate contributes to basic pH during curing, bioactivity, minimum microleakage, long-term stability and strength.

The early properties are, however, not unaffected by the CA part. The setting time and film thickness (film thickness is one of the most important properties of a dental luting cement) is influenced by the CA. The poly acrylic acid (PAA) has a dual function in this hybrid material. Besides functioning as in a conventional GIC being cross linked by leaking $Ca^{2+}$ ions from the glass and building up the solid body, the poly acrylic acid also has an important role as a dispersing agent for the CA. The tartaric acid (TAA) is added in order to control the setting of the GIC, as used for conventional glass ionomers. It will also additionally change the setting behaviour of the CA by retarding it. The TAA and PAA also have an additional advantageous effect on the shelf life of the product. A pure calcium aluminate product would be extremely moisture sensitive and would show a shelf life that is mainly depending on the humidity conditions during manufacturing. The hybrid GIC-CA of the invention would have the same kind of dependency, but to a much lesser extent. The TAA and PAA create a low pH which prevents the adsorbed moisture in the powder from reacting with the CA, which would otherwise reduce the early reactivity of the CA.

According to the invention the $Ca^{2+}$ scavenging chelating agent, such as $Na_3$-NTA, is added to the liquid in order to control the setting of the material and, in turn, to be able to achieve low film thickness values. The $Na_3$-NTA is a chelating agent and works by scavenging $Ca^{2+}$ ions. This retards the setting mechanism of both the CA and the GIC and allows for achieving thin films, but at the same time a setting time that is acceptable.

Other substances than $Na_3$-NTA may be used as the $Ca^{2+}$ scavenging chelating agent. There are several chelating agents that would give similar effects, such as sodium salts of TAA (tartaric acid), EDTA (ethylenediamine tetraacetic acid), citric acid and possibly other chelating agents that scavenge $Ca^{2+}$ ions. The pH of the added chelating agent is important. Both the NTA and the tartaric acid are available as either partially neutralized or fully neutralized acids. The pH will change depending on the acid of choice. The fully neutralized acids have a neutral pH and affect the setting only by changing the $Ca^{2+}$ ion balance. If a partially neutralized acid is used, the lower pH of this compound will also affect the setting and produce thin films, but also a much longer setting. Another function of the additions of the neutralized chelating agents is as a dispersion agent creating an optimal viscosity of the material.

Thus, two binding phases may work at separate time or work over-lapped in the over-all setting and hardening process facilitating the combination of early improved mouldability with high performance end features mainly related to stability and mechanical properties.

The system and material according to the invention have the advantages as compared to systems/materials such as glass ionomer cements or monomer based filling materials, of being highly mouldable, hydrophobic, bioactive, non-shrinking and in having stable long-term properties.

The system and material according to the present invention yields stable thin layers with minimal microleakage. Like the material disclosed in WO 2005/039508, the present material solidifies in at least two steps, i.e. by cross-linking of the polycarboxylic or salt thereof and by hydration

EXAMPLES

Description of Raw Materials and Preparation

1. The calcium aluminate $(CaO)(Al_2O_3)$ used was synthesised and treated according to the description below.
2. A reactive, acid soluble strontium-fluoro-silicate glass produced by Dentsply DeTrey, Konstanz, Germany.
3. Poly acrylic acid, p.a. quality, having an average molecular weight of more than 5,000.
4. Tartaric acid, laboratory quality.
5. Strontium fluoride, p.a. quality, milled to the specified particle size distribution with a $d(99)_V$ of <12 µm.
6. LiCl was used either as crystals or pre-prepared standard solutions, p.a. quality.
7. Neutralised Nitrilo tri acetic acid ($Na_3$-NTA), either as crystals, powders or pre-prepared standard solutions were used.
8. Deionised water. (The water should be treated so that the main part of its ion content has been removed. The water could also preferably be further treated in order to remove microorganisms and other impurities)

Example 1

Preparation of the Powder

The calcium aluminate used for this material is synthesised using high purity $Al_2O_3$ and either of CaO and $CaCO_3$. The correct amount of the raw materials are weighed in to a suitable container (1:1 molar ratio). The powders are intimately mixed by tumbling in excess isopropanol or tumbled dry using a dry powder mixer. If mixing in isopropanol is performed the next step will be removing the isopropanol, such as by evaporation of the solvent using an evaporator combining vacuum and heat and finally a heating oven. The next step is filling high purity $Al_2O_3$ crucibles with the powder mix and heat treating it above 1300° C. for the appropriate amount of time in order to get nearly mono phase calcium aluminate according to the description above. After heat treatment the material is crushed using a high energy crusher, in this case a roller crusher with alumina rollers. After crushing the calcium aluminate is milled to the specified particle size distribution with a $d(99)_V$ of <12 µm.

The final powder formulation is obtained in the following way: All powder components are weighed in with high accuracy according to the composition in table 1.

TABLE 1

Composition of the final powder formulation.

| Raw material | Wt % |
| --- | --- |
| Calcium aluminate | 47.50 |
| Polyacrylic acid | 11.42 |
| Tartaric acid | 1.84 |
| Alumino-fluoro-silicate glass | 34.24 |
| Strontium fluoride | 5.00 |

The components are weighed into a glass beaker, and the beaker is thereafter placed in a dry mixer and the components mixed at medium speed for 3 hours. The next step after mixing is sieving through a 125 µm sieve in order to homogenise the powder and remove large agglomerates. After sieving the powder is transferred to a suitable container, sealed and stored dry. The powder is now ready for use.

Example 3

Preparation of the Liquid

The LiCl is first dried at 150° C. for at least 2 hours in order to remove physically bound water. The LiCl and the $Na_3$-NTA are weighed into a PE bottle so that the final composition after addition of the water will be 18 mM of LiCl and 0.3 wt % of $Na_3$-NTA. After the water has been added the bottle is shaken until all the salts have dissolved. The liquid is now ready for use.

Example 4

Description of Tests

The powder and liquid described above were tested together in the below tests using a powder to liquid (P:L) ratio of 3.2:1. The material is either mixed by hand using a spatula by bringing the required amount of powder and liquid on to a mixing pad and mixing them thoroughly for 35 seconds, or by means of a capsule system. In the later case the powder and liquid have been pre-filled, in correct amounts to generate the required P:L ratio, into a dental capsule system. Several different designs of such systems exist and anyone of these may be used. The capsule is first activated by bringing the powder and liquid together. The capsule is then transferred to a capsule mixing machine and mixed for a sufficient period of time. Using a 3M/ESPE Rotomix the time should be 8 s with a 3 s centrifuge stage in the end. After mixing the ready material is dispensed using a therefore suited tool, into any desired sample mould or container. There is no significant difference in properties depending on whether the material is mixed by hand, or using a capsule system.

The tests performed on the material are the tests shown in table 2.

TABLE 2

| Test | Controlling standard |
| --- | --- |
| Net setting time | ISO 9917:2003 part 1 |
| Film thickness | ISO 9917:2003 part 1 |
| Compressive strength | ISO 9917:2003 part 1 |
| Acid erosion | ISO 9917:2003 part 1 |
| Radio Opacity | ISO 9917:2003 part 2 |
| In vitro bioactivity | N/A |

The results show that by producing a dental cement according to the above description and using it with a P:L ratio of 3.2:1 all the above tests according to ISO 9917:2003 are fulfilled. Regarding the bioactivity, it has been shown by means of energy dispersive spectroscopy (EDS), scanning electron microscopy (SEM), transmission electron microscopy (TEM), grazing incidence X-ray diffraction (GI-XRD) that a layer of crystallised hydroxyl apatite is formed on the surface of the material when submerged in phosphate buffered saline (PBS) for a period of 7 days.

Example 5

A series of tests was performed to investigate the influence of adding a chelating agent to the hydration liquid. The chelating agents tested were $Na_3$-NTA, $Na_2$-TAA and EDTA, respectively. All the liquid additives was added in the range mentioned above into deionised water and with a fixed amount of LiCl added. A pure 18 mM LiCl solution was used as a reference, in addition one liquid with no LiCl added was tested. The parameters tested as response were Film thickness, Net setting time and Compressive strength, all according to the ISO 9917:2003 part 1. All liquids were tested using a powder with the composition as described in Example 1 and a P:L ratio of 3.2:1. The composition of the liquid tested is shown in Table 3.

TABLE 3

Composition of the liquids tested

| Liquid nr | LiCl (mM) | $Na_3$-NTA (wt %) | $Na_2$-TAA (wt %) | EDTA (wt %) |
|---|---|---|---|---|
| 1 | 18 | | | |
| 2 | 18 | 0.3 | | |
| 3 | 18 | 1 | | |
| 4 | — | 0.3 | | |
| 5 | 18 | | 0.3 | |
| 6 | | | 1 | |
| 7 | | | | 0.3 |
| 8 | | | | 1 |

Description of Tests

The tests performed were Net setting time (ST), Film thickness (Ft) and compressive strength (CS), all according to ISO 9917:2003 part 1. The results are shown in Table 4 and demonstrate that the addition of a chelating agent clearly has an effect on both setting time and film thickness. If too much chelating agent is added the setting time becomes a bit too long, as is also the case when EDTA is added. The tests also show that an addition of LiCl is necessary in order to get sufficient compressive strength. All results are mean values of at least 6 samples.

TABLE 4 results from tests with chelating agents

| Liquid nr | ST (min) | Ft (μm) | CS (MPa) |
|---|---|---|---|
| 1 | 4 | 30 | 160 |
| 2 | 4.5 | 16 | 144 |
| 3 | 6.18 | 14 | 147 |
| 4 | 4.5 | 18 | 70 |
| 5 | 5 | 23 | 150 |
| 6 | 7 | 20 | 132 |
| 7 | 8.38 | 15 | 120 |
| 8 | >10 | 15 | 116 |

Example 6

A series of tests was performed to investigate the influence of the P:L ratio on the basic physical properties. P:L ratios ranging from 2.0:1 up to 4.0:1 were tested. In the range of 3.0:1-3.7:1, every 0.1 step was tested. The properties measured were ST, Ft and CS and the powder and liquid used were the ones presented in Example 1 above. All tests were performed according to ISO 9917:2003 part 1. The results of the tests are shown in Table 5.

TABLE 5

Results from the P:L ratio tests.

| P:L | ST (min) | Ft (μm) | CS (MPa) |
|---|---|---|---|
| 2.0:1 | 7.9 | 10 | 90 |
| 2.5:1 | 5.5 | 12 | 120 |
| 3.0:1 | 4.5 | 13 | 150 |
| 3.1:1 | 4.58 | 15 | 155 |
| 3.2:1 | 4.65 | 14 | 170 |
| 3.3:1 | 4.7 | 12 | 167 |
| 3.4:1 | 4.5 | 16 | 169 |
| 3.5:1 | 4.44 | 15 | 174 |
| 3.6:1 | 4.40 | 13 | 180 |
| 3.7:1 | 4.37 | 19 | 181 |
| 3.9:1 | 4.1 | 21 | 183 |
| 4.0:1 | 3.60 | 24 | 185 |

The results demonstrate that there is a range of P:L ratios between 3.0:1 up to 3.6:1 or 3.7:1 within which the three basic, and very important physical parameters of ST, Ft and CS are very stable. This is a key feature in order for a powder and liquid based material to be used together with a capsule based mixing and dispensing system.

The invention is not limited to the embodiments described, but can be varied within the scope of the claims.

The invention claimed is:

1. A composition comprising (a) a powdered cement comprising 40-60 wt % of calcium aluminate, 8-15 wt % of poly acrylic acid, 0.5-5 wt % of tartaric acid, 25-45 wt % of strontium-fluoro-alumino-silicate glass, and 2.5-10 wt % of strontium fluoride; and (b) an aqueous hydration liquid based on de-ionized water.

2. The composition of claim 1, wherein the aqueous hydration liquid additionally contains LiCl.

3. The composition of claim 1, wherein the ratio of powdered cement to aqueous hydration liquid is from 2.0:1 up to 4.3:1.

4. The composition of claim 2, wherein the ratio of powdered cement to aqueous hydration liquid is from 2.0:1 up to 4.3:1.

5. A powdered cement for use in the composition of claim 1 comprising 40-60 wt % of calcium aluminate, 8-15 wt % of poly acrylic acid, 0.5-5 wt % of tar-tarc acid, 25-45 wt % of strontium-fluoro-alumino-silicate glass, and 2.5-10 wt % of strontium fluoride.

6. The powdered cement of claim 5, comprising 47-68 wt % of calcium aluminate, 11-12 wt % of poly acrylic acid, 1.5-2.0 wt % of tartaric acid, 33-35 wt % of strontium-fluoro-alumino-silicate glass, and 4-6 wt % of strontium fluoride.

7. The powdered cement of claim 6, wherein the calcium aluminate has a particle size below 12 μm with a mean particle size in the range of 1.5-4 μm.

8. The powdered cement of claim 5, wherein the calcium aluminate has a particle size below 12 μm with a mean particle size in the range of 1.5-4 μm.

9. A hydration liquid for use in the composition of claim 1, comprising 98-100 wt % of deionised water, 10-200 mM of LiCl, and 0.1-2 wt % of a $Ca^{2+}$ scavenging chelating agent.

10. The hydration liquid of claim 9, wherein the $Ca^{2+}$ scavenging chelating agent is selected from the group consisting of partially or fully neutralized acids.

11. The hydration liquid of claim 10, wherein the partially or fully neutralized acids are sodium salts of said acids.

12. The hydration liquid of claim 11 comprising 10-200 mM of LiCl, 0.2-0.4 wt % of tri sodium nitrilo tri acetic acid, and deionised water to 100%.

13. The hydration liquid of claim 10, comprising 10-200 mM of LiCl, 0.2-0.4 wt % of tri sodium nitrilo tri acetic acid, and deionised water to 100%.

14. The hydration liquid of claim 9, comprising 10-200 mM of LiCl, 0.2-0.4 wt % of tri sodium nitrilo tri acetic acid, and deionised water to 100%.

15. A kit comprising the composition of claim 1.

16. A kit comprising the composition of claim 2.

17. A kit comprising the composition of claim 3.

18. A capsule mixing system comprising the composition of claim 1.

19. A capsule mixing system comprising the composition of claim 2.

20. A capsule mixing system comprising the composition of claim 3.

21. A method of using the composition of claim 1 for cementation of an implant to another implant and/or to tooth or bone tissue.

22. The composition according to claim 2, wherein LiCl is present in the aqueous hydration liquid in a concentration of 10-200 mM.

23. The composition according to claim 3, wherein the ratio of powered cement to aqueous hydration liquid is from 3.0:1 to 3.7:1.

24. The composition according to claim 3, wherein the ratio of powdered cement to aqueous hydration liquid is from 3.0:1 to 3.6:1.

25. The composition according to claim 4, wherein the ratio of powered cement to aqueous hydration liquid is from 3.0:1 to 3.7:1.

26. The composition according to claim 4, wherein the ratio of powdered cement to aqueous hydration liquid is from 3.0:1 to 3.6:1.

27. The hydration liquid according to claim 10, wherein the partially or fully neutralized acids comprise partially or fully neutralized tartaric acid, ethylenediamine tetraacetic acid (EDTA), citric acid and nitrilo tri acetic acid (NTA), or a mixture thereof.

* * * * *